United States Patent [19]
Lehle et al.

[11] Patent Number: 5,798,226
[45] Date of Patent: Aug. 25, 1998

[54] YEAST HOST STRAINS WITH DEFECTS IN N-GLYCOSYLATION

[75] Inventors: Ludwig Lehle, Regensburg; Klaus Lehnert, Hammersbach; Erhard Kopetzki, Penzberg, all of Germany

[73] Assignee: Boehringer Mannheim GmbH, Mannheim, Germany

[21] Appl. No.: 651,323

[22] Filed: May 31, 1996

Related U.S. Application Data

[63] Continuation of Ser. No. 104,436, Aug. 9, 1993, abandoned.

[30] Foreign Application Priority Data

Aug. 7, 1992 [DE] Germany .......................... 42 26 094.9
Jan. 23, 1993 [DE] Germany .......................... 43 01 932.3

[51] Int. Cl.$^6$ .............................. C12N 1/19; C12N 1/18; C12N 15/67; C12P 21/00
[52] U.S. Cl. .................. 435/69.1; 435/71.1; 435/171; 435/172.1; 435/172.3; 435/255.2; 435/255.21
[58] Field of Search ............................ 435/259.21, 69.1, 435/172.3, 255.2, 255.21, 71.1, 171, 172.1

[56] References Cited

FOREIGN PATENT DOCUMENTS

| | | |
|---|---|---|
| 0314096 | 10/1988 | European Pat. Off. . |
| 0314096 | 5/1989 | European Pat. Off. . |
| 0344864 | 12/1989 | European Pat. Off. . |
| 0415565 | 7/1990 | European Pat. Off. . |
| 0382332 | 8/1990 | European Pat. Off. . |
| 8912675 | 12/1989 | WIPO . |

OTHER PUBLICATIONS

Hitzeman et al., Nucl. Acids Res., 11:2745–2762 (1983).
Wood et al., Nature, 314:446–449 (1985).
Green et al., J. Biol. Chem., 261(16):7558–7565 (1986).
Nagasu et al., "Isolation of New Temperature–Sensitive Mutants of *Saccharomyces cerevisae* Deficient in Mannose Outer Chain Elongation", Yeast, vol. 8: 535–547 (1992).
Nakayama et al., "OCH1 encodes a novel membrane bound mannosyl–transferase: outer chain elongation of asparagine–linked oligo–saccharides", EMBO Journal, vol. 11, No. 7, pp. 2511–2519, (1992).
Kopetzki et al. "Enzymes in Diagnostics:Achievements and Possibilities of Recombinant DNA Technology", Clin. Chem 40/5: 688–704, (1994).
Huffaker et al. Temperature Sensitive Yeast Mutants Deficient in Asparagine–linked Glycosylation, The Journal of Biological Chem., vol. 257, No. 6, Mar. 25, pp. 3203–3210, 1982.
Hirschberg et al., Selection of Mutant Chinese Hamster Ovary Cells Altered in Glycoproteins by Means of Tritiated Fucose Suicide, Molecular and Cellular Biology, Oct. 1981, pp. 02–909.
Bekkers, A.C.A.P.A; Franken, P.A.F.; Van den Bergh, C.J.; Verbakel, J.M.A.; Verheij, H.M.; De Haas, G.H.: The use of genetic engineering to obtain efficient production of porcine pancreatic phospholipase A2 by *Saccharomyces cerevisiae*. Biochim. Biophys. Acta 1089, 345–351 (1991).

Ballou, L.; Cohen, R.E.; Ballou, C.E.: *Saccharomyces cerivisiae* mutants that make mannoproteins with a truncated carbohydrate outer chain. J. Biol. Chem. 255, 5986–2991 (1980).

Ballou, C.E.: Yeast cell wall and cell surface. In: Strathern, J.N.; Jones, E.W.; Broach, J.R. (eds.), The Molecular Biology of the Yeast Saccharomyces, Metabolism and Gene Expression, Cold Spring Harbor Laboratory, New York, pp. 335–360 (1982).

Ballour, L.; Alvardo, E.; Tsai, P.; Bell, A; Ballou, C.E.: Protein glycosylation defects in the *Saccharomyces cerevisiae* mnn7 mutant class. J. Biol. Chem. 264, 11857–11864 (1989).

Ballou, C.E.: Isolation characterization, and properties of *Saccharomyces cerevisiae* mmn mutants with nonconditional protein glycosylation defects. Methods Enzymol. 185, 440–470 (1990).

Ballou, L.; Hitzeman, R.A.; Lewis, M.S.; Ballou, C.S.: Vanadate–resistant yeast mutants are defective in protein glycosylation. Proc. Natl. Acad. Sci. 88, 3209–3212, (1991).

Beggs, J.D.: Transformation of yeast by a replicating hybrid plasmid. Nature 275, 104–109 (1978).

Carlson, M.; Taussig, R.; Kustu, S.; Botstein, D.: The secreted form of invertase in *saccharomyces cerevisiae* is synthesized from mRNA encoding a signal sequence. Mol. Cell. Biol. 3, 439–447 (1983).

Ciriacy, M.: Genetics of alcohol dehyrdogenase in *Saccharomyces cerevisiae*. I. Isolation and genetic analysis of ad–mutants. Mut. Res. 29, 315–326 (1975).

De Baetselier, A.; Vasavada, A.; Dohet, P.; Ha–Ti, V.; De Beukelaer, M.; M.; Erpicum, T.; De Clerk, L.; Hanotier, J.; Rosenberg, S.: Fermentation of yeast producing A. niger glucose oxidase: scale up, purification and characterization of the recombinant enzyme. Biotechnology 9, 559–561 (1991).

Delorme, E.: Transformation of *saccharomyces cerevisiae* by electroporation. Applied and Environmental Microbiology 55, 2242–2246 (1989).

Dijken, J.P. van; Veenhuis M.: Cytochemical localization of glucose oxidase in peroxisomes of *Aspergillus niger*. European J. Appln. Microbiol. Biotechnol. 9, 275–283 (1980).

(List continued on next page.)

*Primary Examiner*—Johnny F. Railey, II
*Attorney, Agent, or Firm*—Felfe & Lynch

[57] ABSTRACT

Saccharomyces mutants with defects in N-glycosylation which are obtainable by [$^3$H]-mannose suicide selection, introduction of one or several selective markers, selection of those strains which, after transformation with the plasmid YEpL/glucose oxidase, secrete 10 mg/l glucose oxidase or more into the culture medium after culture under standard conditions, are allelic to the ngd mutations in *Saccharomyces cerevisiae*, DSM 7042, DSM 7338, DSM 7160 and/or 7340 and express proteins with a uniform carbohydrate structure.

35 Claims, 3 Drawing Sheets

OTHER PUBLICATIONS

Erhart, E.; Hollenberg, C.P.: The presence of a defective LEU2 gene on 2uDNA recombinant plasmids of *saccharomyces cerevisiae* is responsible for curing and and high copy number. J. Bacteriol. 156, 625–635 (1983).

Frederick, K.R.; Tung, J.; Emerick, R.S.; Masiarz, F.R.; Chamberlain, S.H.; Vasavada, A.; Rosenberg, S.; Chakraborty, S.; Schopter, L.M.; Massey, N.: Glucose oxidase from *Aspergillus niger*. J. Biol. Chem. 265, 3793–3802 (1990).

Hadwick, K.G.; Lewis, M.j.; Semenza, J.; Dean, N.; Pelham, H.R.B.: ERD1, a yeast gene required for the retention of luminal endoplasmic reticulum proteins, affects glycoprotein processing in the Golgi apparatus. EMBO J. 9, 623–630 (1990).

Haselbeck, A.; Hosel, W.: Studies on the effect of the incubation conditions, various detergents and protein concentration on the enzymatic activity of N-glycosidase F (glycopeptidase F) and endoglycosidase F. Topics in Biochemistry 8, 1–4 (1988).

Hochuli, E.; Doebeli, H.; Schacher, A.: New metal chelate adsorbent selective for proteins and peptides containing neighbouring histidine residues. J. Chromatography 411, 177–184 (1987).

Hochuli, E.; Bannworth, W.; Doebeli, H.; Genz, R.; Stueber, D.: Genetic approach to facilitate purification of recombinant proteins with a novel metal chelate adsorbent. Biotechnology 6, 1321–1325 (1988).

Huffaker, T.C.; Robbins, P.W.: Yeast mutants deficient in protein glycosylation. Proc. Natl. Acad. Sci. 80, 7466–7470 (1983).

Innis, M.A.: Glycosylation of heterologous proteins in *saccharomyces cerevisiae*. In: Barr, P.J.; Brake, A.J.; Valenzuela, P. (eds.), Yeast genetic engineering. Butterworths, Stoneham, Mass, pp. 233–246 (1989).

Ito, H.; Jukuda, A.; Murata, K.; Kimura, A: Transformation of intact yeast cells treated with alkali cations. J. Bacteriol. 153, 163–168 (1983).

Kopetzki, E.; Buckel, P.; Schumacher, G.: Cloning and characterization of baker's yeast alpha glucosidase: overexpression in a yeast strain devoid of vacuolar proteinases. Yeast 5, 11–24 (1989).

Kornfeld, R.; Kornfeld, S.: Assembly of asparagine–linked oligosaccharides. Ann. Rev. Biochem. 54, 631–664 (1985).

Kukuruzinska, M.A.; Bergh, M.L.E.; Jackson, B.J.: Protein glycosylation in yeast. Ann. Rev. Biochem. 56, 915–944 (1987).

Kriechbaum, M.; Heilmann, H.J.; Wientjes, F.J; Han, M.; Jany, K.–D.; Gassen, H.G.; Sharif, F.; Alaeddinoglu, G.: Clonig and DNA sequence analysis of the glucose oxidase gene from *Aspergillus niger* NRRL–3. FEBS Lett. 255, 63–66 (1989).

Laemmli, U.K.: Cleavage of structural proteins during the assembly of the head of bacteriophage T4. Nature 227, 680–685 (1970).

Maniatis, T. et al., In: Molecular cloning: A laboratory manual. Cold Springs Harbor Laboratory Press, Cold Spring Harbor, New York (1989).

Moir, D.T.: Yeast mutants with increased secretion efficiency. In: Barr, P.J.; Brake, A.J.; Valenzuela, P. (eds.), Yeast genetic engineering, Butterworths. Stoneham. Mass, pp. 215–231 (1989).

Mullis, K.B.; Faloona, F.A.: Specific synthesis of DNA in vitro via a poly–merase–catalyzed chain reaction. Methods Enzymol. 155, 335–360 (19870.

Nakano, A.; Muramatsu, M.: A novel GTP–binding protein. Sarpl. is involved in transport form the endoplasmic reticulum to the Golgi apparatus. J. Cell. Biol. 109, 2677–2691 (1989).

Newman, A.P.; Ferro–Novick, S.: Characterization of new mutants in the early part of the yeast secretory pathway isolated by |3H| mannose suicide selection. J. Cell. Biol. 105, 1587–1594 (1987).

Novick, P.; Field, C.; Schekman, R.: Identification of 23 complementation groups required for post–translational events in the yeast secretory pathway. Cell 21, 205–215 (1980).

Paulson, C.P.: Glycoproteins: what are the sugar chains for? TIBS 14, 272–276 (1989).

Rudolph, H.K., Antebi, A.; Fink, G.R.; buckley, C.M.; Dorman, T.E.; LeVitre, J.; Davidow, L.S.; Mao, J.; Moir, D.T.: The yeast secretory pathway is perturbed by mutations in PMR1, a member of a Ca2+ ATPase family. Cell 58, 133–145 (1989).

Reddy, V.A.; Johnson, R.S.; Biemann, K.; Williams, R.S.; Ziegler, F.D.; Trimble, R.B.; Maley, F.: Characterization of glycosylation sites in yeast external invertase. I. N–linked oligosaccharide content of the individual sequons. J. Biol. Chem. 263, 6978–6985 (1988).

Runge, K.W.; Robbins, P.W.: *Saccharomyces cerevisiae* mutants in the early stages of protein glycosylation. In: Bonventre, P.F.; Morello, J.A.M.; Silver, S.D.; Wu, H.C. (eds), Microbiology—1986. American Society for Microbiology, Washington, D.C. pp. 312–316 (1986).

Schekman, R.; Novick, P.: The secretory process and yeast cell–surface assembly. In: Strathern, J.N.; Jones, E.W.; Broach, J.R. (eds.), The Molecular Biology of the yeast saccharomyces, metabolism and gene expression, Cold Spring Harbor Laboratory, New York. pp. 361–398 (1982).

Schmitt, H.D.; Wagner, P.; Pfaff, E.; Gallwitz, D.: The ras–related YPT1 gene product in yeast: a GTP–binding protein that might be involved in microtubule organization. Cell 47, 401–412 (1986).

Schmitt, H.D.; Puzichia, M.; Gallwitz, D.: Study of a temperature–sensitive mutant of teh ras–related YPT1 gene product in yeast suggests a role in the regulation of intracellular calcium. Cell 53, 635–647 91988).

Sherman, F.; Fink, G.R.; Hicks, J.B.: Methods in Yeast Genetics: A Laboratory Manual, Cold Spring Harbor Laboratory, Cold Spring Harbor, New York, (1981).

Tanner, W.; Lehle, L.: Protein glycosylation in yeast. Biochim. Biophys. Acta 906, 81–99 (1987).

Warren, C.E.: Glycosylation–considerations for protein engineering. BFE 7, 392–395 (1990).

Whittington, H.; Kerry–Williams, S.; Bidgood, K.; Dodsworth, N. Peberdy, J.; Dobson, M.; Hinchliffe, E.; Ballance, D.J.: Expression of the *Aspergillus niger* glucose oxidase gene in A. niger, A. nidulans and *saccharomyces cerevisiae*. Curr. Genet. 18, 531–536 (1990).

Zamenhof, S.: Prepartion and assay of deoxyribonucleic acid from animal tissue. Methods Enzymol. 3, 696–704 (1957).

Ziegler, F.D.; Maley, F.; Trimble, R.B.: Characterization of glycosylation sites in yeast external invertase. II. Location of the endo–betta–N–acetylglucosaminidase H–resistant sequons. J. Biol. Chem. 263, 6978–6985 (1988).

YEAST HOST STRAINS WITH DEFECTS IN N-GLYCOSYLATION

This application is a continuation of application Ser. No. 08/104,436, filed Aug. 9, 1993, now abandoned.

The present invention concerns yeast host strains with defects in N-glycosylation as well as their use for the expression of uniformly glycosylated proteins.

There are three ways in which a protein can be provided posttranslationally with carbohydrates. A distinction is made between:

N-glycosylation
  N-glycosidic linking of the carbohydrate chain to Asn
O-glycosylation
  O-glycosidic linking of the carbohydrate chain to Thr or Ser
glycosyl-phosphatidyl-inositolanchor (GPI)
  component of some membrane proteins,
  the GPI anchor serves to embed them in the phospholipid membrane.

The glycosylation of proteins is described for example in:
Kukuruzinska, M. A. et al., Ann. Rev. Biochem. 56 (1987) 915–944;
Paulson, C. P., TIBS 14 (1989) 272–276;
Warren, C. E., BFE 7 (1990) 392–395;
Ballou, C. E., In: Strathern, J. N., et al., The Molecular Biology of the Yeast Saccharomyces, Cold Spring Harbor Laboratory, New York, pp. 355–360 (1982).
Kornfeld, R.; Kornfeld, S., Ann. Rev. Biochem 54 (1985) 631–664;
Tanner, W.; Lehle, L., Biochim. Biophys. Acta 906 (1987) 81–99;
Innis, M. A., In: Barr, P. J. et al., Yeast genetic engineering, Butterworths, Stoneham, Mass., pp. 233–246 (1989).

The O-glycosidic carbohydrate structures of yeast proteins consist of an unbranched mannose chain of 1–5 mannose residues. The O-glycosylation begins in the ER (transfer of the first mannose residue) and is completed in the Golgi apparatus.

N-glycosylation takes place in two steps. A core unit of N-acetylglucosamine, mannose and glucose is built up on a lipid carrier intermediate and this is transferred in the ER onto Asn residues of glycoproteins. After the protein-bound core unit has been processed (cleavage of the glucose residues and a specific mannose residue in the ER), the sugar structure is elongated in the Golgi apparatus ("outer chain" glycosylation). The structure of the outer chain glycosylation is specific to the organism.

The outer chain glycosylation of secreted yeast proteins is of the high mannose type i.e. it is composed of a long polymannose oligosaccharide chain. Proteins which are secreted heterologously in yeast are also provided with this yeast-specific outer chain glycosylation of the high mannose type which is also denoted hyperglycosylation. In many cases this is undesired since it results in the formation of a heterogeneous protein product (carbohydrate part, molecular weight). Moreover the heterogeneous carbohydrate part may complicate the protein purification. The hyperglycosylation may impede the posttranslational processing (e.g. maturation of a "prepro" protein to form the native protein by proteolytic cleavage of the prepro segment) for steric reasons or reduce the cleavage efficiency (Bekkers, A.C.A.P.A. et al., Biochim. Biophys. Acta 1089 (1991) 345–351). In addition the specific activity (in units/units of weight) of hyperglycosylated enzymes is lowered by the increased portion of carbohydrate. Moreover the yeast-specific outer chain glycosylation is strongly immunogenic which is undesirable in a therapeutic application.

Glucose oxidase from Aspergillus niger is a naturally secreted N-glycosylated homodimer (molecular weight/subunit (SU): ca. 80 kDa, cofactor: 1 FAD/SU, 1 SS bridge/SU). gulcose oxidase expressed heterologously in Saccharomyces cerevisiae is secreted very efficiently into the medium. The enzyme is enzymatically active but heterogeneous with regard to the carbohydrate part and molecular weight due to a non-uniform outer chain glycosylation of up to 150 mannose residues. In contrast glucose oxidase isolated from A. niger has a relatively uniform carbohydrate structure (core glycosylation).

Kriechbaum, M. et al., FEBS Lett. 255 (1989) 63–66;
Frederick, K. R. et al., J. Biol. Chem. 265 (1990) 3793–3802;
De Baetselier, A. et al., Biotechnology 9 (1991) 559–561;
Whittington, H. et al., Curr. Genet. 18 (1990) 531–536;
Rosenberg, S., WO 89/12675;

In addition glucose oxidase expressed/secreted in yeast has a lower specific activity (units/g enzyme) due to hyperglycosylation in comparison to the enzyme isolated from A. niger. The glucose oxidase secreted in A. niger has a relatively uniform carbohydrate structure (core-like glycosylation, molecular weight/SU: ca. 80 kDa).

The N-glycosylation of secreted yeast proteins is also usually not uniform. This is for example known for external S. cerevisiae invertase (Reddy, V. A. et al., J. Biol. Chem. 263 (1988) 6978–6985; Ziegler, F. D. et al., Biol. Chem. 263 (1988) 6978–6985). Of the 14 potential sequons (sequon, glycosylation site, amino acid sequence pattern: Asn-X-Ser/Thr) of the invertase, 13 are either completely or partially glycosylated. However, only 9–10 of the 13 sequons that are used per invertase subunit are glycosylated on average. A sequon defined by the protein sequence can either i) always be glycosylated, ii) never be glycosylated or iii) only sometimes be glycosylated.

In addition a defined sequon either has a short oligosaccharide chain ($GlcNAc_2Man_{8-15}$) or a long polymannose oligosaccharide chain ($GlcNAc_2Man_{50-100}$). The observed heterogeneous N-glycosylation of invertase is caused by:

i) only a partial glycosylation of the potentially used sequons per molecule (e.g. only 3 or 5 potentially used sequons are glycosylated purely at random), ii) the presence of short core oligosaccharides and long polymannose chains (outer chain) and, iii) variation of the "outer chain" chain length.

The following procedures are known for obtaining glycoproteins with a reduced portion of or lack of carbohydrate i.e. with a uniform carbohydrate part:

expression of the glycoprotein coding gene in the presence of inhibitors of glycosylation (e.g. tunicamycin) or of vesicle transport (e.g. Brefeldin A).

Enzymatic deglycosylation of proteins in vitro e.g. with endo F or/and endo H or/and N-glycosidase F Removal/alteration of glycosylation sites by mutagenesis at the DNA level.

Use of host strains with defects in glycosylation.

Yeast mutants with changes in N-glycosylation are known. A distinction is made between secretion mutants with blocked secretion and mutants which secrete proteins with altered N-glycosylation.

Secretion mutants have a localized block in the secretion machinery as a result of which incompletely N-glycosylated proteins accumulate in the corresponding cell compartment. e.g.

sec mutants ("secretion defective") by R. Schekman,
Novick, P. et al., Cell 21 (1980) 205–215;
Schekman, R. and Novick, P., In: Strathern, J. N. et al.,
The Molecular Biology of the Yeast Saccharomyces.
Cold Spring Harbor Laboratory, New York, pp.
361–398 (1982);

bet mutants ("blocked early in transport") by S. Ferro-Novick,
Ferro-Novick, S. and Newman A. P., J. Cell. Biol. 105
(1987) 1587–1594;

ypt1 mutant by D. Gallwitz,
Schmitt, H. D. et al., Cell 47 (1986) 401–412;
Schmitt, H. D. et al., Cell 53 (1988) 635–647;

sar1 mutants by M. Muramatsu,
Nakano, A. and Muramatsu, M., J. Cell. Biol. 109
(1989) 2677–2691.

Mutants with defects in N-glycosylation usually have a functioning secretion path. Defective N-glycosylation can be caused by different gene defects such as e.g. mutations in the carbohydrate building (modifying) enzyme system, in the cellular protein transport system ("sorting, targeting").

In sorting and targeting mutants the Golgi apparatus or partial areas of the Golgi apparatus which is the cell compartment in which inter alia the outer chain glycosylation reactions take place is for example circumvented in a bypass during the secretion of proteins.

mnn mutans (mannan defective) by C. E. Ballou,
Ballou, L. et al., J. Biol. Chem. 255 (1980) 5986–5891;
Ballou, C. E., Methods Enzymol. 185 (1990) 440–470;
Ballou, C. E., In: Strathern, J. N. et al., The Molecular
Biology of the Yeast Saccharomyces. Cold Spring
Harbor Laboratory, New York, pp. 355–360 (1982);

vrg mutants (vanadate resistant glycosylation) by C. E. Ballou,
Ballou, L. et al. Proc. Natl. Acad. Sci. 88 (1991)
3209–3212;

alg mutants (asparagine-linked glycosylation defective)
by R. Robbins,
Huffaker, T. C. and Robbins, P. W., Proc. Natl. Acad.
Sci. 80 (1983) 7466–7470;
Runge, K. W. and Robbins, P. W., In: Bonventre, P. F.
et al., Microbiology, American Society for
Microbiology, Washington, D.C. pp. 312–316
(1986);

pmr1 (ssc1) mutants by G. Fink, (D. T. Moir),
Duncan, M. J. and Smith, R. A., EPA 0211208;
Fink, G. R., EPA 0382332;
Rudolph, H. K. et al., Cell 58 (1989) 133–145;

erd1 mutants (endoplasmatic reticulum retention defective) by H. R. B. Pelham,
Hardwick, K. G. et al., EMBO J. 9 (1990) 630–632.

Mutants with a block in the secretion path are understandably unsuitable for biotechnological purposes (homologous and heterologous secretion of proteins).

Many of the N-glycosylation-defective mutants are conditionally lethal i.e. they are not viable under normal conditions (culture temperature 30° C.) and have a temperature sensitive (ts) phenotype such as e.g. the mutants alg1, alg2, alg4, bet1, bet2, almost all sec mutants and ypt1 (cold sensitive).

A temperature sensitive phenotype means that the lethal ts mutation is only expressed after a temperature shift of e.g. 26° C. (permissive growth conditions) to 37° C. (non-permissive growth conditions). These mutants are also understandably less suitable for biotechnological purposes. A mutant group which is characterized by an outer chain glycosylation which is substantially reduced (mnn7, mnn8, mnn10) or almost completely absent or by modified "core" glycosylation (mnn9) has the following disadvantages: cell growth slows down, the cells are morphologically changed and already lyse during the culture so that these mutants can only be grown in osmotically stabilized media (addition of ca. 0.5M KCl or ca. 1M sorbitol).

Moreover some of the N-glycosylation-defective mutants (e.g. alg1) described in the literature have a defect which is only partially expressed in the cell ("leaky"). This leads to a heterogeneous N-glycosylation (contamination, superimposed by wild-type N-glycosylation).

Yeast strains which are able to express/secrete proteins with shortened or absent outer chain N-glycosylation are described for example in EP-A 0 344 864. The strains described in this application are all based on the mnn9 mutation described by C. E. Ballou. Mnn9 mutant strains are susceptible to lysis during growth and must therefore be osmotically stabilized (see above).

The yeast strains described in EP-A 0 314 096 are also based on the mnn 9 mutation. The strains were improved with regard to lysis sensitivity to such an extent that osmotic stabilizers can be omitted from the medium.

The MNN9 gene was cloned for this and subsequently strains were constructed in which the MNN9 gene is under the control of a promoter which can be regulated externally. This for example enables sufficient active MNN9 gene product to be present during the culture phase of the cells for the synthesis of necessary cellular glycosylated host proteins and by this means the mnn9 mutation is only expressed in the actual production phase of the desired N-hypoglycosylated protein. However, this method has the following drawbacks:

The cell culture is much more complicated.

After reaching the desired cell density the MNN9 gene has to be switched off, for example by a temperature shift of the culture, before inducing synthesis of the desired N-hypoglycosylated protein After switching off the MNN9 gene the cells have the mnn9 phenotype i.e. grow poorly etc. (see above).

Active MNN9 gene product which is still present can lead to the synthesis of small amounts of the undesired hyperglycosylated protein product despite the switching off of the MNN9 gene when product synthesis has already been induced.

Furthermore it is known that yeast secretion mutants (supersecretion mutants) often secrete hypoglycosylated glycoproteins. Such an example is described in EP-A 0 382 332.

The molecular cause of the ssc1 (pmr1) mutation is very probably based on the inactivation of a D-type ATPase which is involved in vesicle transport between ER and the Golgi complex. It is presumed that the sorting mechanism of the cell is impaired by the destruction of the SSC1 gene which results in the opening of an alternative secretion path bypassing the Golgi compartment in which the outer chain glycosylation usually takes place.

Disadvantages of the ssc1 mutation are in particular:

The ssc1 mutation causes a calcium-dependent growth. The mutant strains grow poorly at a lower calcium concentration.

The increased secretion (e.g.: prochymosin, u-PA and t-PA) is dependent on the gene product. The heterologous secretion of α-1 antitrypsin and the secretion of homologous enzymes (invertase into the periplasma and alkaline phosphatase, proteinase B and carboxypeptidase Y into the vacuole) is not increased (Moir, D. T., In: Barr, P. J.; Brake, A. J. et al., Yeast genetic engineering, Butterworths, Stoneham, Mass., pp. 215–231 (1989).

The object of the present invention was to avoid these disadvantages and to provide yeast host strains which grow well for the homologous and heterologous secretion of proteins with an N-glycosylation which is as uniform and as low as possible (e.g. with a complete or partial defect in outer chain glycosylation) since there is a need in biotechnology for yeast strains for the homologous and heterologous secretion of proteins with uniform, defined N-glycosylation which grow well and secrete well.

This object is achieved by yeast mutants with defects in N-glycosylation (ngd mutants, N-glycosylation-defective) which can be obtained by [$^3$H]-mannose suicide selection, introduction of one or several selective markers (auxotrophy requirements and/or resistances) and selection of those strains which, after transformation with the plasmid YEpL/ glucose oxidase and culture in complete medium with 2% yeast extract, 4% Bactopeptone, Difco, 0.1 mol/l phosphate buffer pH 7.0, 1 % fructose and 6% maltose, produce glucose oxidase in an amount of 10 mg/l or more after 3–4 days incubation while shaking and are allelic to Saccharomyces cerevisiae DSM 7042, DSM 7160, DSM 7338 and/or DSM 7340.

The principle of [$^3$H]-mannose suicide selection consists essentially of:

Mutagenesis (of a wild-type strain, e.g. X2180-1A; ATCC 26786)

Incubation with [$^3$H]-mannose

Concentration of hyperglycosylation-defective mutants by storing the cells at low temperatures, preferably at about −80° C., until the survival rate of the cells decreases to $10^2$–$10^3$ of the original value, the storage period for this is preferably two to four months.

Selection of mutants with reduced N-glycosylation on the basis of homologously expressed invertase.

Analysis of secreted invertase by activity staining and/or immunoprecipitation and determination of the molecular weight of the invertase preferably by SDS-PAGE. The extent of glycosylation can be determined from the determined molecular weight.

[$^3$H]-mannose suicide selection is an effective method for the production and isolation of yeast mutants (Littlwood, B. S., In: Methods of Cell Biology, Prescott, D. M. (ed), Academic Press, New York, (1975) vol. IX, pp. 273–285). In this method cell death is brought about in some of the yeast cells by tritium-labelled mannose which is for example incorporated into glycoproteins of the cell. In surviving cells there is for example a change in carbohydrate metabolism and/or glycoprotein synthesis (Pouyssegur, J., Proc. Natl. Acad. Sci. 77, 2698–2701 (1980); Hirschberg, C. B. et al., Mol. Cell. Biol. 1 (1981), 902–909; Huffaker, T. C. and Robbins, P. W., J. Biol. Chem. 257 (1982), 3202–3210. [$^3$H]-mannose suicide selection was chosen to obtain mutants which contain a defect in outer chain glycosylation of yeast mannoproteins. In doing so the assumption was that glycosylation-defective mutants incorporate less readioactive mannose than wild-type cells and therefore exhibit an increased resistance to exposition with [$^3$H]-mannose. In order to avoid unspecificities in this process which are based on the metabolism of mannose, it is preferable to use mannose which is derivatized with tritium at position 2.

The selectable markers (auxotrophy markers and/or resistances) can be introduced by crossing the yeast strains to form diploids (isolation of the zygotes by micromanipulation) and optionally subsequent sporulation to haploids (tetrad analysis). Suitable selectable markers are for example the auxotrophy markers ura3, leu2, trp1, lys2, his3, his4 and ade2 or genes which produce resistance, e.g. to copper (CUP1 gene) or G418 (Tn601(903) aminoglycoside phosphotransferase gene) (Bitter, G. A. et al., Methods Enzymol. 153 (1987) 516–543).

The N-glycosylation-defective mutants preferably contain a defect in the NGD29 and/or NGD62 gene.

The ngd phenotype can be determined by activity staining of invertase by means of native PAGE gels using sucrose and 2,3,4-trinitrophenyltetrazolium chloride as substrate/glucose reagent.

An adequate production of glucose oxidase can be determined by determining the activity of glucose oxidase secreted into the medium after culture under standard conditions. For this the strain to be tested (glucose oxidase transformant) is incubated in complete medium for 3–4 days while shaking preferably after a selective pre-culture. Yeast extract, Bactopeptone, fructose and maltose are preferably added to the complete medium at neutral pH.

The determination of glucose oxidase is for example carried out according to the method described in the examples under "general methods".

Mutants according to the present invention (allelic mutants) can be determined by a test in which it is analyzed whether the mutants to be examined have a mutation in the same genes as the yeast strains DSM 7042 or DSM 7338 (ngd29) and DSM 7160 or DSM 7340 (ngd62).

For this each of the strains to be tested is crossed with a yeast strain from the DSM 7042/7338 group and the DSM 7160/7340 group and the diploid strains obtained in this way are analyzed.

The mutation (strain) to be tested is allelic to the ngd mutants (DSM 7042, DSM 7338, ngd29) according to the present invention and/or (DSM 71606 DSM 7340, ngd62) when the mutations do not compensate in diploid cells.

The mutation (strain) to be tested is not allelic to the ngd mutants (DSM 7042, DSM 7338, ngd29) according to the present invention and/or (DSM 7160, ngd62) when the mutations complement each other in the diploid cell and a wild-type phenotype results with regard to N-glycosylation.

Preferred yeast strains used according to the present invention are the strains DSM 7042, DSM 7160, DSM 7338 and/or DSM 7340. DSM 7338 and/or DSM 7340 are particularly preferably used.

The present invention also concerns a process for the production of Saccharomyces mutants with defects in N-glycosylation by [$^3$H]-mannose suicide selection, introduction of one or several selectable markers (auxotrophy requirements and/or resistance genes) and selection of those strains which, after transformation with the plasmid YEpL/ glucose oxidase and fermentation in complete medium containing 2% yeast extract, 4% Bactopeptone, Difco, 0.1 mol/l phosphate buffer pH 7.0, 1% fructose and 6% maltose, produce glucose oxidase in an amount of more than 10 mg/l after 3–4 days incubation while shaking and are allelic to Saccharomyces cerevisiae DSM 7042, DSM 7160, DSM 7338 and/or DSM 7340.

The present invention additionally concerns the use of the yeast strains according to the present invention for the production of proteins which are essentially uniformly glycosylated. In order to produce yeast-specific glycoproteins (e.g. external invertase, acid phosphatase, endoglucanase and cell wall mannoproteins) the yeast strains according to the present invention are fermented and the desired glycoprotein is isolated from the cells or from the culture supernatant according to known methods and purified.

Heterologous proteins are obtained by transforming yeast strains according to the present invention with a recombinant DNA which contains the gene for the glycoprotein to be expressed. Glucose oxidase, α1-microglobulin, erythropoietin and glucoamylase can for example be produced in this way.

The present invention in addition concerns a process for the expression and production of proteins which are essentially uniformly glycosylated by transformation of a yeast mutant defective in N-glycosylation and allelic to the strain DSM 7042, DSM 7338, DSM 7160, or DSM 7340, with a DNA coding for the protein, fermentation of the transformants and isolation of the protein from the cells or the culture supernatant.

For patent purposes the following were deposited at the "Deutsche Sammlung für Mikroorganismen (DSM), Mascheroder Weg 1 B, D-3300 Braunschweig:

| | | Deposit number | Deposit date |
|---|---|---|---|
| 1. | Plasmid YEpL | DSM 7038 | 07.04.1992 |
| 2. | Yeast mutant BMY3-9A (ngd29) | DSM 7042 | 08.04.1992 |
| 3. | Yeast mutant BMY3-9C (ngd29) | DSM 7193 | 24.07.1992 |
| 4. | Yeast mutant BMY12-20D (ngd62) | DSM 7160 | 09.07.1992 |
| 5. | Yeast mutant BMY8-12A (ngd62) | DSM 7157 | 09.07.1992 |
| 6. | Yeast mutant BMY13-7B (mnn9) | DSM 7158 | 09.07.1992 |
| 7. | Yeast mutant BMY13-1C (mnn9) | DSM 7159 | 09.07.1992 |
| 8. | Yeast mutant JM 1935 | DSM 7156 | 09.07.1992 |
| 9. | Yeast mutant DBY 746 | DSM 4316 | 14.12.1987 |
| 10. | Yeast mutant N-BMY3-9A | DSM 7338 | 08.12.1992 |
| 11. | Yeast mutant N-BMY13-1C | DSM 7339 | 08.12.1992 |
| 12. | Yeast mutant N-BMY12-20D | DSM 7340 | 08.12.1992 |
| 13. | Yeast mutant BMY3-9C | DSM 7341 | 08.12.1992 |

The following examples elucidate the invention further.

EXAMPLES

General methods
Recombinant DNA technique

Standard methods were used to manipulate DNA such as those described by Maniatis, T. et al., in: Molecular cloning: A laboratory manual. Cold Spring Harbor Laboratory Press, Cold Spring Harbor, N.Y., (1989). The molecular biological reagents used were used according to the manufacturer's instructions.

Yeast transformation

*Saccharomyces cerevisiae* strains were transformed according to the method of Beggs, J. D. (Nature 275 (1978) 104–109; Ito, H. et al., J. Bacteriol. 153 (1983) 163–168 or Delorme, E. (Applied and Environmental Microbiology 55 (1989) 2242–2246). Fructose was used instead of glucose as a C source for yeast strains expressing glucose oxidase.

Determination of glucose oxidase activity

The determination of glucose oxidase activity was carried out at 25° C. in a volume of 1 ml in 0.1 mol/l potassium phosphate buffer, pH 7.0 saturated with oxygen containing 0.18 mol/l glucose, 15 units/ml horseradish peroxidase and 1.75 mmol/l ABTS® glucose reagent. The reaction was started by addition of glucose oxidase (10 µl sample containing glucose oxidase diluted to 5–20 mU/ml) and the change in absorbance/min (ΔA/min) was determined at 405 nm ($\epsilon_{405}$=36.8 [mmol$^{-1}$×l×cm$^{-1}$]). 1 unit (U) glucose oxidase activity is defined as the amount of enzyme which oxidizes 1 µmol glucose per min at 25° C. The specific activity of purified *A. niger* glucose oxidase is ca. 230 U/mg protein under these test conditions.

Protein determinations

The protein determination was carried out by the microbiuret method (Zamenhof, S. et al., Methods Enzymol. 3 (1957) 696–704) with bovine serum albumin as standard.

The protein concentration of purified GOD enzymes was calculated on the basis of the optical density at 280 nm (1 $OD_{280}$=1.5 mg/ml purified glucose oxidase ).

Cell lysis and isolation of crude extract

The cells from 5 ml culture medium (ca. 0.1–0.2 g yeast, wet weight) were centrifuged down. The cell pellet was washed once with 10 mmol/l phosphate buffer, pH 7.0 and subsequently lysed with glass beads by homogenization with a Whirlmix (Ciriacy, M., Mut. Res. 29 (1975) 315–326). Afterwards the cells were resuspended/extracted in 2 ml 10 mmol/l phosphate buffer, pH 7.0, the cell debris was removed by centrifugation and the supernatant was processed further as a crude extract.

SDS polyacrylamide gel electrophoresis (SDS-PAGE)

Soluble samples (medium supernatants and cell lysates) were admixed with 1/5 volumes 5×SDS sample buffer (1×SDS sample buffer: 50 mmol/l Tris-HCl, pH 6.8, 1% SDS, 1% mercaptoethanol, 10% glycerol, 0.001% bromophenol blue) and incubated for 5 min at 95° C. Non-soluble proteins of the cell debris fraction were extracted with 2 ml 1×SDS sample buffer and 6–8 mol/l urea, denatured by heating for 5 minutes to 95° C. and separated from insoluble components by centrifugation. Afterwards the proteins were separated by SDS-PAGE (Laemmli, U. K., Nature 227 (1970) 680–685) and stained with Coomassie Brilliant Blue® dye.

Example 1

Construction of plasmids for the secretion of *A. niger* glucose oxidase in *S. cerevisiae*

Construction of the yeast expression vector YEpL (starting vector)

Plasmid YEpL is based on the α-glucosidase vector YEp/5C6b3 (Kopetzki et al., Yeast 5 (1989) 11–24; Kopetzki, et al., EP-A 0 323 838). See FIG. 1. The ca. 2.3 kBp long EcoRI/PvuII fragment from the plasmid pBR322 (plasmid origin, ampicillin resistance gene) serves to replicate the plasmid in *E. coli*. For replication in yeast the vector contains the ca. 2.2 kBp long EcoRI fragment from the 2 µm DNA of the yeast (subcloned from the *E. coli*/yeast shuttle vector YEp24). In addition the vector contains the URA3 and LEU2d gene in order to select the plasmid in auxotrophic yeast strains and an α-glucosidase expression cassette (GLUCPI gene). It consists of the α-glucosidase promoter, a polylinker (cloning site for the genes to be expressed) and the α-glucosidase terminator. In addition the MAL2-8cp gene is present the gene product of which, the MAL2-8cp protein, activates the α-glucosidase promoter. The α-glucosidase promoter is repressed in the presence of glucose. It derepresses after consumption of the glucose and achieves its maximum activity after induction with maltose.

1.1 Construction of plasmid YEp/KL6b3

Figure 1:
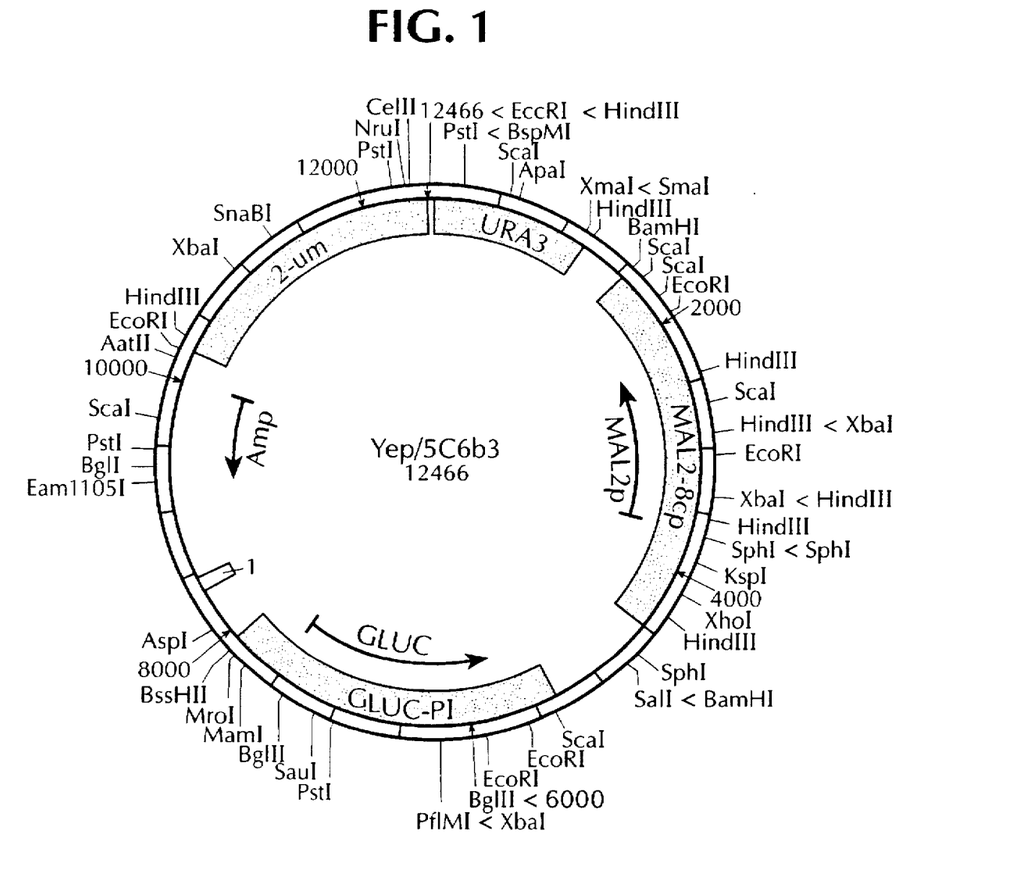
FIGS. 1–3 are plasmids YEp/Sc6b3: YEpL and YEpL/glucose oxidase, respectively.

The ca. 1.4 kBp long DNA sequence which is not required between the α-glucosidase terminator and the MAL2-8cp promoter was deleted from the plasmid YEp/5C6b3 (FIG. 1).

For this the plasmid YEp/5C6b3 was linearised with XhoI, the 5' overhanging ends were filled up with Klenow polymerase, the plasmid was re-cleaved with MroI and the 8.7 kBp long MroI/XhoI (blunt) vector fragment was isolated. In a second preparation the plasmid YEp/5C6b3 was digested with the restriction endonucleases MroI and ScaI, the 2.5 kBp long MroI/ScaI fragment containing the α-glucosidase gene was isolated and ligated with the 8.7 kBp long MroI/XhoI(blunt) vector fragment. The desired plasmid was identified by restriction mapping and designated YEp/KL-6b3.

1.2 Construction of plasmid YEp/KL-6b3M

A MluI-linger (5'-GACGCGTC-3') was ligated into the SspI restriction endonuclease cleavage site of the 5' non-translated region of the MAL2-8cp gene. Plasmid construction: YEp/KL-6b3M.

1.3 Construction of plasmid YEp/KL-6b3M-MCS

The structural gene of α-glucosidase was removed by the "polymerase chain reaction" (PCR) technique (Mullis, K. B. and Faloona, F. A., Methods in Enzymol. 155 (1987) 335–350) and replaced by a DNA linker (multicloning site, MCS).

For this the GLUCPI promoter sequence from the plasmid YEp/KL-6b3M was amplified by means of PCR using the primer pair:

Primer (1) (SEQ ID NO. 1): 5'-ATTTCTCCT-TATTGCGCGCTT-3'

Primer (2) (SEQ ID NO. 2): 5'-TCTATTCAGCTGTCGA-CATAGATCTTATGTAATTTAGTTACGCTTGAC-3' and the ca. 410 Bp long PCR product was isolated by agarose gel electrophoresis.

The GLUCPI terminator sequence from the plasmid YEp/KL-6b3M was amplified in a second PCR reaction using the primer pair:

Primer (3) (SEQ ID NO. 3): 5'-AGATCT-ATGTCGACAGCTGAATAGATAAAATTAGTGC-GGACTTTTTTTTA-3'

Primer (4) (SEQ ID NO. 4): 5'-GTCATTTGTAAAGTAAAATTCCAA-3' and the ca. 860 Bp long PCR product was isolated by agarose gel electrophoresis.

Afterwards equimolar amounts (ca. 50 pg of each) of the isolated PCR fragments were combined in the PCR reaction mixture, incubated for 5 min at 95° C. to denature the ds-DNA, the reaction mixture was cooled to 60° C. to anneal the complementary singular DNA strands containing MCS, the hybridization products were converted into ds-DNA using Taq polymerase and amplified in a third PCR reaction using the primer pair:

Primer (1) (SEQ ID NO. 1): 5'-ATTTCTCCTTATTGCGCGCTT-3'

Primer (4) (SEQ ID NO. 4): 5'-GTCATTTGTAAAGTAAAATTCCAA-3'.

Afterwards the ca. 1.27 kBp long PCR product was digested with the restriction endonucleases MroI and MluI, the ca. 0.92 kBp long MroI/MluI-GLUPI-promoter/MCS/GLUCPI terminator fragment was isolated by agarose gel electrophoresis and ligated into the ca.8.55 kBp long MroI/MluI-YEp/KL-6b3M vector fragment. The desired plasmid YEp/KL-6b3M-MCS was identified by means of restriction mapping and the DNA regions synthesized by means of PCR were checked by DNA sequencing.

1.4 Construction of the plasmid YEpL

Figure 2:
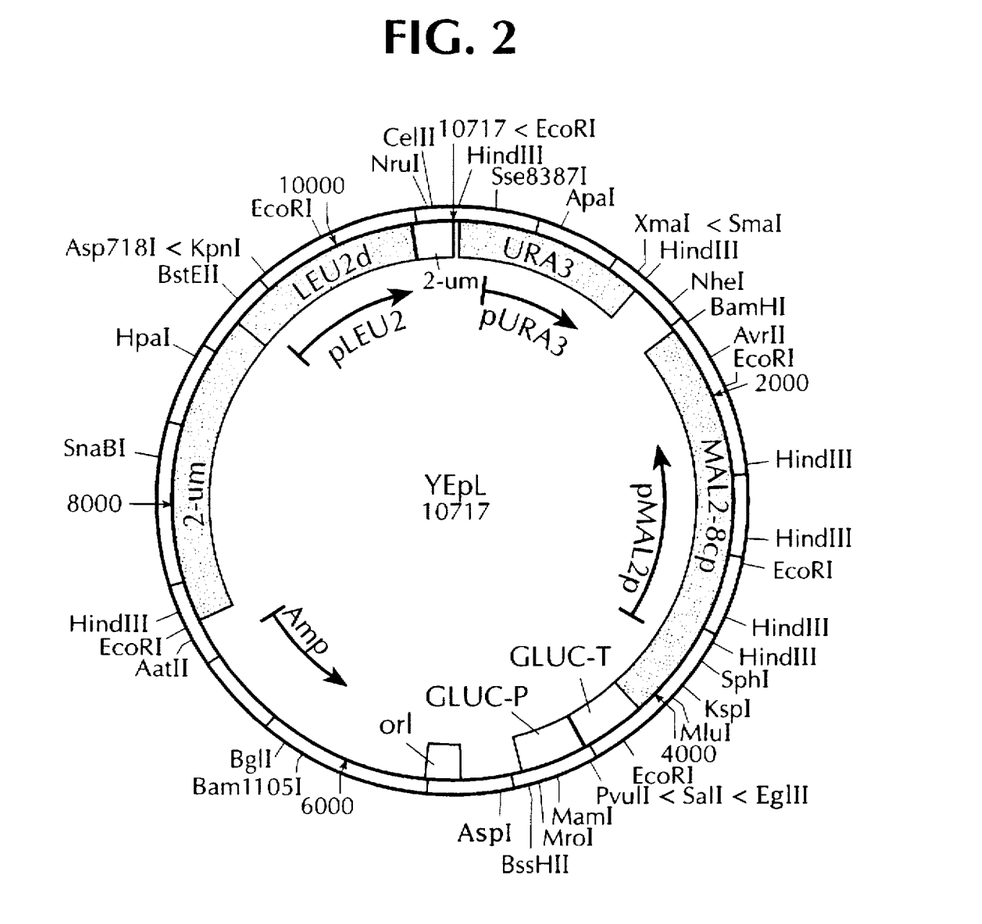

In the following plasmid construction the LEU2d gene was inserted into the plasmid YEp/KL-6b3M-MCS. For this the plasmid YEp/KL-6B3M-MCS was digested with CelII and SnaBI and the 8.4 kBp long CelII/ScaBI-YEp/KL-6b3M-MCS vector fragment was isolated. The LEU2d gene was isolated as a ca. 2.32 kBp long CelII/SnaBI fragment from the plasmid pADH040-2 (Erhart, E. and Hollenberg, C. P., J. Bacteriol. 156 (1983) 625–635) and ligated with the 8.4 kBp long CelII/SnaBI-YEp/KL-6b3M-MCS vector fragment. The desired plasmid construction YEpL (DSM 7038) was identified by restriction mapping. See FIG. 2.

1.5 Construction of the plasmid YEpL/glucose oxidase

The cloning of the glucose oxidase gene used (strain: NRRL-3, ATTC 9029), subcloning in the pBluescript SK(+) vector, DNA sequencing and deduction of the glucose oxidase protein sequence are described in the publication by Kriechbaum, M. et al. (FEBS Lett. 255 (1989) 63–66). The glucose oxidase gene was cloned in 2 partial regions (SalI restriction fragments) in pBluescript SK(+).

The plasmid pSK/glucose oxidase 1.8 contains a ca. 1.8 kBp long SalI fragment which codes for the 5'- non-translated region and N-terminal region of the glucose oxidase structural gene up to the SalI cleavage site at Bp position 164 (Bp position corresponds to the numbering by Kriechbaum, M. et al). The plasmid pSK/glucose oxidase 2.0 contains a ca. 2.0 kBp long SalI fragment which codes for the remainder of the glucose oxidase structural gene from Bp position 165 to 1853 as well as for the 3'- non-translated region downstream of the glucose oxidase structural gene.

The 5' and 3'-non-translated region of the glucose oxidase gene was removed by means of the PCR technique, the glucose oxidase structural gene was provided with singular restriction endonuclease cleavage sites (BglII and PvuII) and in addition a singular SphI and NheI cleavage site was introduced into the C-terminal coding region of the glucose oxidase structural gene while maintaining a DNA sequence coding for the native glucose oxidase protein. Subsequently the GOD structural gene was assembled from the two PCR fragments in a three-fragment ligation and inserted into the vector YEpL. The following primer pair: was used to amplify the N-terminal glucose oxidase structural gene and plasmid pSK/glucose oxidase 1.8 was used as template DNA.

Primer (5)(SEQ ID NO.5): 5'-GCCCGGTACCAGATCTATGCAGACTCTCCTTGTGAGCT-3'
                                            BglII Primer (6)(SEQ ID NO.6): 5' -TCTAGAACTAGTGGATCCCCC-3'

The following primer pair was used to amplify the remaining glucose oxidase structural gene and plasmid pSK/glucose oxidase 2.0 was used as template DNA.

Primer (7)(SEQ ID NO.7): 5' -GCCGGCGAACGTGGCGAGAA-3'

Figure 3:
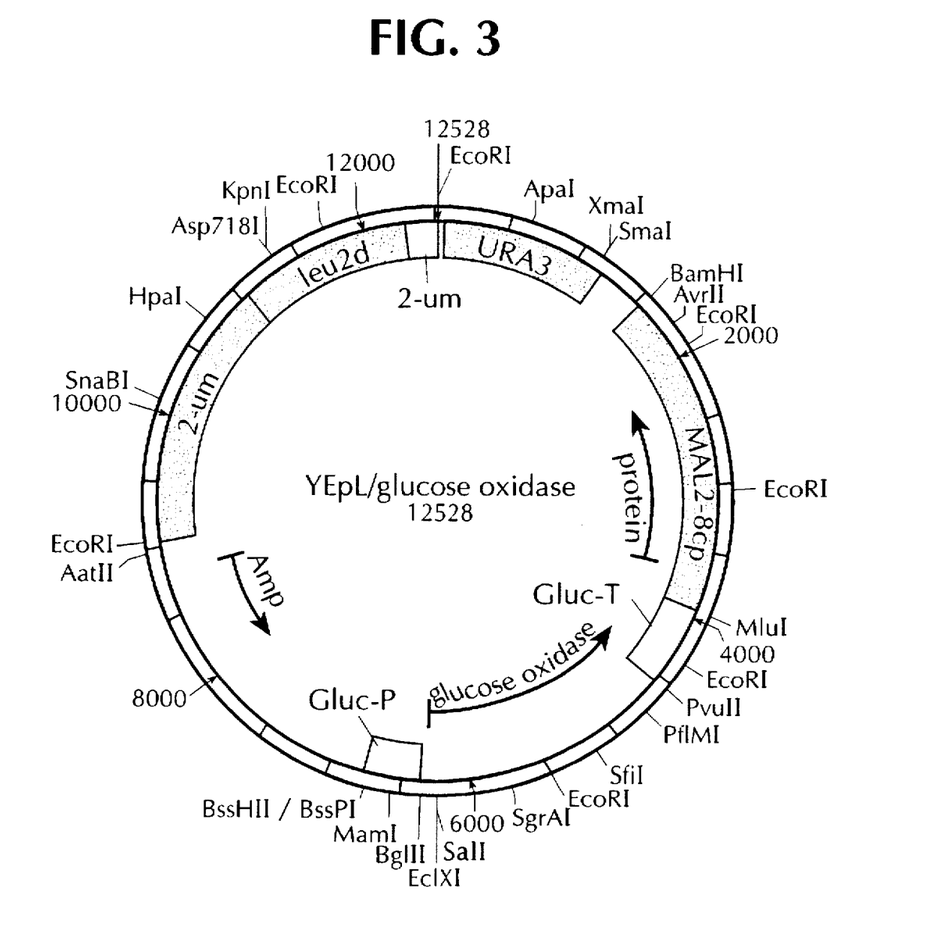

Primer (8)(SEQ ID NO.8): 5' -ATATATCAGCTGTCACTGCATGCTAGCATAATCTTCCAAGATAGC-3'
                                   PvuII      SphI      NheI The ca. 220 Bp long PCR product of the first reaction was re-cleaved with BglII and SalI and the ca. 130 Bp long BglII/SalI fragment was isolated. The ca. 2.05 kBp long PCR product of the second reaction was digested with SalI and PvuII and the ca. 1.7 kBp long DNA fragment was isolated. Afterwards the PCR fragments were ligated into the ca. 10.7 kBp long BglII/PvuII-YEpL vector fragment (three-fragment ligation). The desired plasmid YEpL/glucose oxidase (FIG. 3) was identified by restriction mapping and partially sequenced (cloning junctions).

1.6 Construction of plasmid YEpL/glucose oxidase (His)4

The plasmid contains a modified glucose oxidase gene which codes for a glucose oxidase enzyme variant that has four additional histidine residues at the C-terminus. YEpL/glucose oxidase (His)4 was produced from the plasmid YEpL/glucose oxidase.

For this the plasmid YEpL/glucose oxidase was partially cleaved with SphI and completely cleaved with PvuII, the ca. 10.7 kBp long SphI/PvuII fragment was isolated and ligated with the following DNA linker prepared from two oligonucleotides by hybridization.

Primer (9)(SEQ ID NO.9): 5'- CAGCACCACCACCACTGACAG-3'
Primer (10)(SEQ ID NO.10):
5'- CTGTCAGTGGTGGTGGTGCTGCATG-3'

SphI
5'-        CAGCACCACCACCACTGACAG-3'
3'-GTACGTCGTGGTGGTGGTGACTGTC-5'
    - - - - Gln His His His His Stop

SEQ ID NO.12

The desired plasmid YEpL/glucose oxidase (His)4 was identified by colony hybridization using radioactively-labelled primer 10 as the probe and further analyzed by restriction mapping and partial sequencing (C-terminal region of the glucose oxidase structural gene).

Example 2

Isolation of yeast host strains with defective N-glycosylation 2.1 [$^H$]-mannose suicide mutagenesis Principle Mutagenesis (starting strain: X2180-1A, genotype: a SUC2 mal mel gal2 CUP1; ATCC 26786
Incubation with [$^3$H]-mannose
Concentration of hyperglycosylation-defective mutants by storing the cells at –80° C. until the survival rate of the cells decreases to $10^2$–$10^3$ (2–4 months)

A yeast strain such as X2180-1A (ATCC 26786) is cultured in YEPD medium (2% Bactopeptone, 1% yeast extract, Difco, and 4% glucose), harvested in the logarithmic growth phase (ca. $5 \times 10^8$ of these cells), washed with 0.1 mol/l sodium phosphate, pH 7 and resuspended in 1.5 ml 0.1 mol/l sodium phosphate, pH 7. The cells are mutagenized by the addition of 0.1 ml ethyl methane-sulfonate for 1 hour at 25° C. 0.2 ml of the cells treated in this way is incubated with 10 ml sodium thiosulfate (5% w/v) for 10 minutes, washed 3× with 0.1 mol/l sodium phosphate, pH 7.0 and resuspended in YEPD medium (2% Bactopeptone, 1% yeast extract, Difco and 4% glucose).

The cells are incubated at 28° C. while shaking until an OD of 0.6 at 578 nm is achieved. $10^6$ cells are washed with YEP medium (2% Bactopeptone, 1% yeast extract, Difco) and resuspended in 0.1 ml YEP with 0.1% glucose. 2 mCi [$^3$H]-mannose (specific activity 18.5 Ci/mmol) is added and the culture is incubated for 60 minutes at 28° C. The cells are centrifuged, washed with water and resuspended in YEPD which contains 25% glycerol and stored at –70° C. for the radioactivity to take effect.

After ca. 45–50 days when the survival rate of the cells has dropped to 1.5–0.2%, aliquots of the cells are plated on YEP agar plates with 2% mannose and incubated at 30° C.

2.2 Isolation of mutants with reduced N-glycosylation

Mutants with a defect in protein glycosylation are firstly selected for their ability not to incorporate [$^3$H]-mannose and to incorporate [$^{35}$S]-methionine. For this the cells are allowed to grow on YEPD agar plates, the yeast colonies are replicated on 2 Rotband filters (Schleicher & Schüll, Dassel, Germany) and the filters are incubated again for 6 hours on YEPD plates. One filter is then incubated in a solution of YEPD (an amount which is just sufficient to wet the filter) which contains 0.01 mCi/ml [$^{35}$S]-methionine. The other filter is impregnated with YEP containing 0.2 mCi/ml [$^3$H]-mannose and incubated for 30 minutes. The cells/colonies are immobilized on the filter with 5% trichloroacetic acid, washed with water and acetone and analyzed by autoradiography.

2.3 Characterization of positive clones by native gel electrophoresis of external invertase The SUC2 gene from *S. cerevisiae* codes for 2 different regulated and compartmented invertase forms, i) a glycosylated invertase which is mainly secreted into the periplasm and ii) an intracellular somewhat shortened non-glycosylated form (Carlson, M. et al., Mol. Cell. Biol. 3 (1983) 439–447). Invertase contains 14 potential N-glycosylation sites of which on average 9–10 are glycosylated in the secreted form per invertase subunit. External wild-type invertase migrates as a diffuse band in native gels due to non-uniform outer chain glycosylation. In contrast the cytoplasmic non-glycosylated form yields a sharp band after activity staining. A change in N-glycosylation can thus be crudely analyzed by means of the migration rate and band sharpness of external invertase in native gels.

The yeast strains (X2180-1A wild-type strain and positive clones) were cultured overnight in 5 ml YEPS medium (1% yeast extract, 2% Bactopeptone, Difco and 2% sucrose), the cells were harvested in the late logarithmic growth phase, washed once with 20 mmol/l sodium azide and lysed with glass beads by homogenization in a Whirlmix. The preparation of cell lysate, the native gel electrophoresis and activity staining of invertase with sucrose and 2,3,4-trinitrophenyltetrazolium chloride as substrate/glucose reagent were carried out according to the method by Ballou C. E. (Methods Enzymol. 185 (1990) 440–470).

The positive clones may be divided into 4 classes on the basis of the invertase activity staining:

1. Mutants with wild-type invertase mobility.
2. Mutants that synthesize neither non-glycosylated nor glycosylated invertase.

3. Mutants with defects in outer chain glycosylation (distinct oligomeric band pattern of 3–4 bands).
4. Mutants which lead to a substantial under-glycosylation of invertase (larger mobility than wild-type invertase).

Results

Mutant strains of class 4, designated ngd29 (DSM 704217338) and ngd62 (DSM 7160/7340) in the following (ngd stands for "N-glycosylation-defective"), synthesized in comparison to the starting strain X2180-1A a uniformly glycosylated dimeric external invertase (sharp bands and increased migration rate in native gels after activity staining). The ngd mutant strains were osmotically stable, could be cultured at 30° C. and did not aggregate during culture.

Example 3

Construction of glycosylation-defective yeast host strains for the expression of homologous and heterologous proteins In order to introduce one or several auxotrophies which can be complemented by transformation, the ngd mutants were crossed with suitable laboratory strains according to the method described by F. Sherman et al. (Methods in Yeast Genetics: A Laboratory Manual, Cold Spring Harbor Laboratory, Cold Spring Harbor, N.Y., (1981)) and diploid strains were isolated by micromanipulation. Subsequently the diploid strains were sporulated and segregants with suitable auxotrophies (e.g. ura3, leu2) and ngd mutation were isolated.

For this the ngd29 mutant was incubated together with the strain DBY746 (MATα ura3-52 leu2-3,-112 trp1-289a his3-Δ1; [DSM 4316] equivalent to ATCC 44733) and the ngd62 mutant was incubated with the JM1935 strain (MATα ura3 leu2 his4, DMS 7156) for 6 hours at 30° C. in YEPD (1% yeast extract, 2% Bactopeptone, Difco, and 2% glucose). Subsequently zygotes were isolated with the aid of a micromanipulator (model according to de Fonbrune from the Bachhofer Company, Reutlingen, Germany) and grown overnight in 5 ml YEPD. The cells were briefly centrifuged, the medium was decanted to about 0.2 ml and the cell pellet was resuspended in the residual medium. This cell suspension was plated on a potassium acetate plate (1% potassium acetate, 1.5% agar). After ca. 5 days the asci obtained in this way were resuspended in 0.5 ml sterile water using an inoculating loop, 10 μl of a β-glucuronidase/aryl sulfatase mixture (Boehringer Mannheim) was added and incubated for 10 min at room temperature. Subsequently 10 ml water was added, the ascus suspension was centrifuged and the supernatant was decanted. The spores of several asci were isolated under a micromanipulator and incubated on YEPD plates (YEPD with 1.5% agar) for 3 days at 30° C. A replica plate was prepared from germinated spores, the colonies were pressed onto synthetic minimal media (0.67% yeast nitrogen base without amino acids, Difco; 2% glucose; 1.5% agar plus additives: 20 mg/l Trp, His, Arg, Met; 30 mg/l Leu, Ile, Lys; 50 mg/l Phe; 100 mg/l Glu, Asp; 400 mg/l Val, Thr, Ser as well as 20 mg/l adenine and uracil; one of these additives was omitted in each of the individual minimal media) and incubated for 3 days at 30° C. Segregants with the ngd29 phenotype which have auxotrophies for uracil and leucine were analyzed/isolated as described in example 2.2. The ngd29 phenotype (as well as the ngd62 phenotype) segregated 2:2 in all examined tetrads, which indicates a single mutation in a single nuclear locus.

Strains BMY3-9A and N-BMY3-9A (MATα leu2-3,112 ura3-52 his3- 1 ngd29; DSM 7042 and DSM 7338) and BMY3-9C and N-BMY3-9C (MATα leu2-3, 112, ura3-52 ngd29; DSM 7193 and DSM 7341) were obtained from the cross DBY746×ngd29 described here.

Strains BMY12-20D and N-BMY12-20D (MATα leu2 ura3 his4 ngd62; DSM 7160 and DSM 7340) were obtained in an analogous manner from the cross JM1935×ngd62.

Example 4

Comparison of the expression/secretion of native *A. niger* glucose oxidase and the glucose oxidase (His)$_4$ variant in wild-type and glycosylation-defective yeast host strains The glucose oxidase from *A. niger* is a naturally secreted glycosylated dimeric enzyme. 8 potential N-glycosylation sites (sequons) and 3 cysteine residues two of which form a disulfide bridge are present on each subunit. In *S. cerevisiae* wild-type strains the expressed glucose oxidase is secreted into the medium and is very heterogeneous with regard to molecular weight due to a non-uniform outer chain glycosylation (hyperglycosylation) (Frederick, K. R. et al., J. Biol. Chem. 265 (1990) 3793–3802; De Baetselier, A. et al., Biotechnology 9 (1991) 559–561; Whittington, H. et al., Curr. Genet. 18 (1990) 531–536). The processed (cleavage of a 22 amino acid long signal sequence) A. niger glucose oxidase protein consists of 583 amino acids with a potential molecular weight of 63 273 Da (Frederick, K. R. et al., J. Biol. Chem. 265 (1990) 3793–3802).

The plasmids YEpL/glucose oxidase (example 1.5) and YEp/glucose oxidase-(His)$_4$ (example 1.6) were transformed in the wild-type strain JM1935 (MATα leu2 ura3 his4 MAL4) DSM 7156 BMY3-9A (DSM 7042 and N-BMY3-9A (DSM 7338) (see example 3) and the transformants were selected on minimal medium agar plates with 1.5% agarose, 0.67% YNB (yeast nitrogen base, salt vitamin mixture, Difco) 0.5% CAA (casamino acids, protein hydrolysate, Difco) and 2% fructose as a C-source (uracil selection).

4.1 Culture of the glucose oxidase transformants

In order to amplify the plasmid copy number (selection for the plasmid coded LEU2d allele; Beggs, J. D., Nature 275 (1978) 104–109; Erhart, E. and Hollenberg, C. P. J., Bacteriol. 156 (1983) 625–635) the transformants were streaked on minimal medium plates without leucine (1.5% agarose, 0.67% YNB, Difco, 60 mg/l adenine and 2% fructose).

Precultures were carried out in leucine selective medium containing 0.67% YNB and 4% fructose in shaking flasks at 30° C. for 48 hours and used to inoculate expression cultures (inoculum: 1–2%). The main culture (1 l shaking culture) was incubated at 30° C. in complete medium containing 2% yeast extract, 4% Bactopeptone, Difco, 0.1 mol/l phosphate buffer, pH 7.0, 1% fructose and 6% maltose for 3–4 days while shaking. Samples were taken after 48 and 72 hours and determinations were made of cell growth (determination of the optical density at 600 nm, $OD_{600}$), the glucose oxidase activity secreted into the medium and residual glucose oxidase activity in the cells was determined in the crude extract after cell lysis.

Expression/secretion analysis of glucose oxidase in the wild-type strain DSM 7156 and the glycosylation-defective host strains DSM 7042/7338 (ngd29)

Plasmid: YEpL/glucose oxidase

| DSM 7156 | glucose oxidase activity (U/ml)/Optical density ($OD_{600}$) Time (hours) | | | |
|---|---|---|---|---|
| | 48 U/ml/$OD_{600}$ | | 72 U/ml/$OD_{600}$ | |
| extracellular | 8 | 13 | 12 | 17 |
| intracellular | 4 | | 6 | |
| total | 12 | | 18 | |
| % secreted | 66 | | 66 | |

Plasmid YEpL/glucose oxidase

| DSM 7042/7338 | glucose oxidase activity (U/ml)/Optical density ($OD_{600}$) Time (hours) | | | |
|---|---|---|---|---|
| | 48 U/ml/$OD_{600}$ | | 72 U/ml/$OD_{600}$ | |
| extracellular | 11 | 9 | 18 | 14 |
| intracellular | 1 | | 2 | |
| total | 12 | | 20 | |
| % secreted | 87 | | 90 | |

Expression/secretion analysis of glucose oxidase in the wild-type strain DSM 7156 and the glycosylation-defective host strains DSM 7042/7338 (ngd29)

Plasmid: YEpL/glucose oxidase $(His)_4$

| DSM 7156 | glucose oxidase activity (U/ml)/Optical density ($OD_{600}$) Time (hours) | | | |
|---|---|---|---|---|
| | 48 U/ml/$OD_{600}$ | | 72 U/ml/$OD_{600}$ | |
| extracellular | 8 | 14 | 9 | 14 |
| intracellular | 5 | | 6 | |
| total | 13 | | 16 | |
| % secreted | 62 | | 58 | |

Plasmid: YEpL/glucose oxidase

| DSM 7042/7338 | glucose oxidase activity (U/ml)/Optical density ($OD_{600}$) Time (hours) | | | |
|---|---|---|---|---|
| | 48 U/ml/$OD_{600}$ | | 72 U/ml/$OD_{600}$ | |
| extracellular | 12 | 10 | 17 | 13 |
| intracellular | 1 | | 1 | |
| total | 13 | | 18 | |
| % secreted | 88 | | 93 | |

Result

No significant differences were found between the glucose oxidase and glucose oxidase $(His)_4$ variant with regard to expression and secretion.

4.2 SDS-PAGE of secreted glucose oxidase

The glucose oxidase $(His)_4$ enzyme expressed (secreted into the medium) in the glycosylation-defective host strains DSM 7042/7338 (ngd29) and DSM 7160/7340 (ngd62) and the enzyme expressed (secreted) in the wild-type strain DSM 7156 and purified glucose oxidase from *A. niger* (Boehringer Mannhein, GFR) were further characterized by SDS-PAGE and subsequent protein staining. The medium supernatants from the wild-type strain containing glucose oxidase were concentrated 10-fold by TCA precipitation before electrophoresis. Carbohydrate-free glucose oxidase $(His)_4$ enzyme was prepared enzymatically using N-glycosidase F and used as a standard for size.

Enzymatic deglycosylation with N-glycosidase F

The deglycosylation was carried out according to the method published by Haselbeck, A. and Hösel, W. (Topics in Biochemistry 8 (1988) 1–4). 0.1 ml medium supernatant containing glucose oxidase $(His)_4$ was precipitated with trichloroacetic acid (final concentration: 10%), the precipitated proteins were centrifuged, the protein pellet was washed with 70% ethanol, dried in a vacuum, taken up in 10 µl 20 mmol/l potassium phosphate buffer, pH 7.2 containing 1% SDS and heated for 3 min. to 95° C. After cooling to room temperature the sample was diluted to 0.1 ml with 20 mmol/l potassium phosphate buffer, pH 7.2, octylglucoside (final concentration: 0.5%) and 5 units N glycosidase F, incubated for 1–12 hours at 37° C. and subsequently 25 µl 5×SDS buffer (see above) was added.

Result

The glucose oxidase enzymes (glucose oxidase and glucose oxidase $(His_4)$) expressed in the glycosylation-defective ngd mutant strains are visible as dominant uniform bands with a molecular weight of ca. 80 kDa in SDS-PAGE gels after protein staining. This experiment shows the absence of outer chain glycosylation in the glucose oxidase enzymes and indicates a uniform core-like glycosylation. With regard to glycosylation the ngd mutant strains have a mnn9-like phenotype. In contrast the glucose oxidase enzymes expressed in wild-type strains are only recognizable as very diffuse bands which cover a molecular weight range of ca. 80–200 kDa.

Example 5

Characterization of the N-glycosylation-defective ngd mutants on the basis of growth on YEPD agar plates with orthovanadate or hygromycin B Glycosylation-defective mutants such as e.g. mnn8, mnn9 and mnn10 show an increased resistance to orthovanadate and an increased sensitivity to the antibiotic hygromycin B. The resistance/sensitivity phenotype enables a differentiation/classification of N-glycosylation-defective mutants (Ballou, L. et al., Proc. Natl. Acad. Sci. 88 (1991) 3209–3212).

The strains to be examined were cultured overnight in YEPD medium (5 ml roller culture) and the strains/cultures were adjusted to an optical density ($OD_{600}$) of exactly 0.05 with YEPD medium. Afterwards 20 µl of each cell suspension was spotted on YEPD agar plates containing 2–15 mmol/l sodium orthovanadate or 10–200 µg/ml hygromycin B. The growth of the cell spots was evaluated after 2 days incubation at 30° C. (see table).

Growth phenotype of yeast cells on YEPD agar plates with sodium orthovanadate or hygromycin B

| Strain | Orthovanadate resistance mmol/1 | | | | | | | | Hygromycin resistance (µg/ml) | | | |
|---|---|---|---|---|---|---|---|---|---|---|---|---|
| | 2 | 3 | 4 | 5 | 6 | 7 | 10 | 15 | 10 | 50 | 100 | 200 |
| DBY 746(wild-type) | + | + | + | + | – | – | – | – | + | + | – | – |
| X2180-1A(wild-type) | + | + | + | + | – | – | – | – | + | + | – | – |
| LB347-1C (mnn9)[1] | + | + | + | + | + | + | + | + | – | – | – | – |
| BMY3-9A (ngd29) | + | + | + | + | + | – | – | – | + | ± | – | – |
| BMY12-20D (ngd62) | + | + | + | ± | – | – | – | – | + | ± | – | – |
| N-BMY3-9A(ngd29) | + | + | + | + | + | – | – | – | + | ± | – | – |
| N-BMY12-20D(ngd62) | + | + | + | ± | – | – | – | – | + | ± | – | – |

+ growth
± very slow growth
– no growth

[1] J. Biol. Chem. 259 (1984) 3805–3811

Result

There are differences between the ngd mutants with regard to resistance pattern which differs from that of the mnn9 mutant and wild-type strains.

Example 6

Characterization/identification of ngd mutants (allelism test)

An allelism test serves to identify (differentiate between) genes and gene defects (mutations). With this technique it is possible to analyze whether 2 mutants are allelic (have a mutation in the same gene). The ngd mutants were examined for allelism among one another and to the mnn9 mutant.

The allelism tests were carried out by means of genetic standard techniques (see: Sherman, F.; Fink, G. R.; Hicks, J. B., Methods in Yeast Genetics: A Laboratory Manual. Cold Spring Harbor Laboratory, Cold Spring Harbor, N.Y., (1981); Guthrie, C. and Fink, G. R. (eds.), Guide to Yeast Genetics and Molecular Biology. Methods Enzymol. 194 (1991)).

Principle

Two haploid mutant strains to be analyzed of different pairing type with auxotrophy requirements that complement each other are crossed and the diploid strains are selected on plates with minimal medium. The diploidism of the isolated strains is confirmed by the presence of DNA sequences specific for the a and α pairing type using PCR analysis in accordance with the method by Huxley, C. et al. (Trends Genet. 6 (1990) 236).

Two mutants are allelic, i.e. have a mutation in the same gene, when the mutations do not complement each other in the diploid cell.

Two mutants are not allelic, i.e. have a mutation in two different genes, when the mutations complement each other in the diploid cell and a wild-type phenotype results.

Strains used:

| | |
|---|---|
| BMY3-9C (MATα leu2-3,-112 ura3-52 ngd29) | DSM 7193 |
| BMY8-12A (MATa trp1-289* his3-Δ1 ngd62) | DSM 7157 |
| BMY13-1C (MATα ura3-52 leu2-3,-112 his3-Δ1 mnn9) | DSM 7159 |
| BMY13-7B (MATa leu2-3,-112 his3-Δ1 mnn9) | DSM 7158 |
| BMY12-20D (MATα leu2 ura3 his4 ngd62) | DSM 7160 |
| N-BMY3-9C (MATα leu2-3,-112 ura3-52 ngd29) | DSM 7341 |
| N-BMY13-1C (MATα ura3-52 leu2-3,-112 his3-Δ1 mnn9) | DSM 7339 |
| N-BMY12-20D (MATα leu2 ura3 his4 ngd62) | DSM 7340 |

| Crossing partners MATα MATa | Phenotype of the haploids | Selection diploids | Phenotype of the diploids |
|---|---|---|---|
| BMY3-9C × BMY8-12A | ngd29xngd62 | his leu | wild-type |
| BMY3-9C × BMY13-7B | ngd29xmnn9 | his ura | wild-type |
| BMY13-1C × BMY8-12A | mnn9xngd62 | trp ura | wild-type |
| BMY12-20D × BMY13-7B | ngd62xmnn9 | his | wild-type |
| N-BMY3-9C × BMY8-12A | ngd29xngd62 | his leu | wild-type |
| N-BMY3-9C × BMY13-7B | ngd29xmnn9 | his ura | wild-type |
| N-BMY13-1C × BMY8-12A | mnn9xngd62 | trp ura | wild-type |
| N-BMY12-20D × BMY13-7B | ngd62xmnn9 | his | wild-type |

SC = synthetic complete medium (0.67% yeast nitrogen base without amino acids, Difco; 2% glucose; 1.5% agar plus additives: 20 mg/l Trp, His, Arg, Met; 30 mg/l Leu, Ile, Lys; 50 mg/l Phe; 100 mg/l Glu, Asp; 400 mg/l Val, Thr, Ser as well as 20 mg/l adenine and uracil; the amino acids Ura, His and Trp were omitted in the individual minimal media as stated in the table in the column headed "Selection of diploids".

Result:

The mutants ngd29 and ngd62 differ from one another and are different from mnn9 (non-allelic).

Example 7

Isolation of glucose oxidase and glucose oxidase (His)$_4$ from wild-type and hyperglycosylation-defective yeast strains 7.1 Isolation of glucose oxidase (His)$_4$ by means of metal chelate chromatography The glucose oxidase variant glucose oxidase (His)$_4$ was isolated using this isolation method from the culture filtrate of BMY3-9A/glucose oxidase (His)$_4$ cells and BMY12-20D/glucose oxidase (His)$_4$ cells (hyperglycosylation-defective host strains).

The culture filtrate was titrated to pH 7.5 with sodium hydroxide and applied to a NTA column equilibrated with 10 mmol/l potassium phosphate buffer, pH 7.5 (column volume 25 ml; NTA gel from the Diagen Company, Düsseldorf; Hochuli, E. et al., J. Chromatography 411 (1987) 177–184; Hochuli, E. et al., Biotechnology 6 (1988) 1321–1325). The column was rewashed with 5–10 column volumes 1 mol/l sodium chloride in 10 mmol/l potassium phosphate buffer, pH 7.5, and with 5–10 column volumes 10 mmol/l potassium phosphate buffer, pH 7.5. Afterwards the glucose oxidase (His)$_4$ enzyme was eluted with 0.1 mol/l imidazole in equilibration buffer, pH 7.5 and the fractions containing glucose oxidase (His)$_4$ (yellow) were dialysed against 10 mmol/l potassium phosphate buffer, pH 7.5.

7.2 Isolation of glucose oxidase and glucose oxidase variants by ion exchange chromatography on O-sepharose ff after previous concentration and dialysis Native glucose oxidase and hyperglycosylated glucose oxidase were purified according to this method.

33 g solid ammonium sulfate (AS saturation concentration 55%) was added to 100 ml sterile-filtered culture filtrate while stirring slowly, the precipitated proteins were centrifuged down after 1-2 hours incubation at room temperature, dissolved in 25 ml 25 mmol/l potassium phosphate buffer, pH 7.5 and dialysed against the same buffer (4×10 l, 24 hours, 4° C.).

Subsequently the dialysate was applied to a Q-sepharose ff column (column volume 12 ml) equilibrated with 25 mmol/l potassium phosphate buffer, pH 7.5 and rewashed with 5-10 column volumes equilibration buffer. The bound glucose oxidase enzymes were eluted by a gradient of 0-1 mol/l KCl in equilibration buffer (ca. 10 column volumes) and the fractions containing glucose oxidase (yellow) were pooled.

Example 8

Biochemical characterization of the isolated glucose oxidase enzymes 8.1 Determination of the specific glucose oxidase activity The determination of glucose oxidase activity is carried out as described in the "general methods" section.

Specific activity of glucose oxidase and glucose oxidase (His)$_4$ expressed in *A. niger, S. cerevisiae* (wild-type) and *S. cerevisiae* (hyperglycosylation-defective mutants)

| Enzyme | Organism/ glycosylation | spec. activity (U/mg protein) | spec. activity (U/mg enzyme) |
|---|---|---|---|
| glucose oxidase | (*A. niger*) | 225 | 195 |
| glucose oxidase | (WT) | 230 | 69 |
| glucose oxidase | (ngd29) | 228 | 196 |
| glucose oxidase | (ngd62) | 213 | 220 |
| glucose oxidase (His)$_4$ | (WT) | 220 | 68 |
| glucose oxidase (His)$_4$ | (ngd29) | 223 | 200 |
| glucose oxidase (His)$_4$ | (ngd62) | 230 | 225 |

*A. niger*, glucose oxidase from *A. niger*, purity II (Boehringer Mannheim)
WT, *S. cerevisiae* wild-type
ngd29, *S. cerevisiae* hyperglycosylation-defective ngd29 mutant
ngd62, *S. cerevisiae* hyperglycosylation-defective ngd62 mutant 8.2 Determination of molecular weight by SDS polyacrylamide gel electrophoresis (SDS-PAGE)

The purified glucose oxidase enzymes were admixed with ⅕ volumes 5×SDS sample buffer (1×SDS sample buffer: 50 mmol/l Tris-HCl, pH 6.8, 1% SDS, 1% mercaptoethanol, 10% glycerol, 0.001% bromophenol blue) and incubated for 5 min at 95° C. Afterwards the proteins were separated by SDS-PAGE (Laemmli, U. K., Nature 227 (1970) 680-685) and stained with Coomassie Brilliant Blue$^R$ dye.

Molecular weight/subunit after SDS-PAGE of glucose oxidase and glucose oxidase (His)$_4$ expressed in *A. niger, S. cerevisiae* (wild-type) and *S. cerevisiae* hyperglycosylation-defective mutants.

| Enzyme | Organism/ glycosylation | Molecular weight/subunit (kDa) |
|---|---|---|
| glucose oxidase | (*A. niger*) | ca. 80 |
| glucose oxidase | (WT) | 80-140 |
| glucose oxidase | (ngd29) | ca. 80 |
| glucose oxidase | (ngd62) | ca. 80 |
| glucose oxidase (His)$_4$ | (WT) | 80-140 |
| glucose oxidase (His)$_4$ | (ngd29) | ca. 80 |
| glucose oxidase (His)$_4$ | (ngd62) | ca. 80 |

*A. niger*, glucose oxidase from *A. niger*, purity II (Boehringer Mannheim)
WT, *S. cerevisiae* wild-type
ngd29, *S. cerevisiae* hyperglycosylation-defective ngd29 mutant
ngd62, *S. cerevisiae* hyperglycosylation-defective ngd62 mutant 8.3 Determination of the portion of carbohydrate (anthrone reaction)

The carbohydrate portion of the glucose oxidase enzymes from different organisms and yeast strains was determined following the method of Ashwell, G. (Methods Enzymol. 3 (1957) 84).

For this 0.5 ml purified glucose oxidase enzyme (concentration 20-100 U/ml in H$_2$O) was mixed with 5 ml anthrone reagent, the solution was incubated for 5 minutes at 25° C. and afterwards heated for 15 minutes in a boiling water bath. After the sample had been cooled to 25° C. the absorbance was determined at 630 nm against a reagent blank. The portion of carbohydrate in the glucose oxidase sample was determined by means of a mannose calibration curve with mannose standard solutions of 5, 25, 75 and 100 μg/ml which was set up at the same time.

Preparation of the anthrone reagent 66 ml concentrated sulfuric acid is carefully diluted with 34 ml water. After cooling to 80° C. 50 mg anthrone and 1 g thiourea are dissolved in the sulfuric acid. The anthrone reagent can be stored for two weeks at 4° C.

Carbohydrate portion of glucose oxidase and glucose oxidase (His)$_4$ expressed in *A. niger, S. cerevisiae* (wild-type) and *S. cerevisiae* (hyperglycosylation-defective mutants)

| Enzyme | Organism/ glycosylation | Carbohydrate portion (%) (relative to protein) |
|---|---|---|
| glucose oxidase | (*A. niger*) | 13 |
| glucose oxidase | (WT) | 71 |
| glucose oxidase | (ngd29) | 12.5 |
| glucose oxidase | (ngd62) | 13 |
| glucose oxidase (His)$_4$ | (WT) | 65 |
| glucose oxidase (His)$_4$ | (ngd29) | 11 |
| glucose oxidase (His)$_4$ | (ngd62) | 12 |

*A. niger*, glucose oxidase from *A. niger*, purity II (Boehringer Mannheim)
WT, *S. cerevisiae* wild-type
ngd29, *S. cerevisiae* hyperglycosylation-defective ngd29 mutant
ngd62, *S. cerevisiae* hyperglycosylation-defective ngd62 mutant

What is claimed is:

1. The isolated yeast strain DSM 7042.
2. The isolated yeast strain DSM 7338.
3. The isolated yeast strain DSM 7160.
4. The isolated yeast strain DSM 7340.
5. A process for the production of a yeast mutant, said process comprising: $^3$H-mannose suicide selection by the introduction of one or several selective markers (auxothrophies and/or resistances), selection of a strain which, after transformation with the plasmid YepL/glucose oxidase and fermentation in complete medium with 2% yeast extract, 4% peptone 0.1 mol/1 phosphate buffer, pH 7.0, 1% fructose and 6% maltose, secretes 10 mg/1 glucose oxidase or more into the medium after 3–4 days incubation while shaking, said strain, when crossed with a strain of Saccharomyces cerevisiae selected from the group consisting of DSM 7042, DSM 7338, DSM 7160 and DSM 7340, yielding a diploid which is defective in outer-chain N-glycosylation, said diploid, when transformed with a DNA expressing a protein of interest, under conditions favoring expression of said protein expressing said protein in hypoglycosylated form substantially without contamination with said protein in a form having outer-chain glycosylation, whereas said protein when expressed in a wild-type strain is expressed in a form having outer-chain glycosylation.
6. A process as claimed in claim 5 wherein said strain is Saccharomyces cerevisiae selected from the group consisting of DSM 7042, DSM 7338, DSM 7160 and DSM 7340.
7. The process according to claim 5, wherein the strain of Saccharomyces cerevisiae is DSM 7042.
8. The process according to claim 5, wherein the strain of Saccharomyces cerevisiae is DSM 7338.
9. The process according to claim 5, wherein the strain of Saccharomyces cerevisiae is DSM 7160.
10. The process according to claim 5, wherein the strain of Saccharomyces cerevisiae is DSM 7340.
11. An isolated mutant yeast strain having defects in outer-chain N-glycosylation, said strain, when crossed with a strain of Saccharomyces cerevisiae selected from the group consisting of DSM 7042, DSM 7338, DSM 7160, and DSM 7340, yielding a diploid having defects in outer-chain N-glycosylation, said diploid, when transformed with a DNA encoding, a protein of interest, under conditions favoring expression of said protein, expressing said protein in hypoglycosylated form substantially without contamination with said protein in a form having GlcNAc2Man$_{50-100}$ glycosylation, wherein said protein, when expressed in a wild-type strain, is expressed in a form having outer-chain glycosylation.
12. The isolated mutant yeast strain according to claim 11, wherein said strain of Saccharomyces cerevisiae is DSM 7042.
13. The isolated mutant yeast strain according to claim 11, wherein said strain of Saccharomyces cerevisiae is DSM 7338.
14. The isolated mutant yeast strain according to claim 11, wherein said strain of Saccharomyces cerevisiae is DSM 7160.
15. The isolated mutant yeast strain according to claim 11, wherein said strain of Saccharomyces cerevisiae is DSM 7340.
16. A method of using the isolated mutant yeast strain according to claim 11 to produce a hypoglycosylated protein of interest, said method comprising fermenting a cell or cells of said strain under conditions to produce a protein of interest in a hypoglycosylated form, and isolating the hypoglycosylated protein of interest from the fermented cell or cells, or from the culture supernatant.
17. A method of using the isolated mutant yeast strain according to claim 12 to produce a hypoglycosylated protein of interest, said method comprising fermenting a cell or cells of said strain under conditions to produce a protein of interest in a hypoglycosylated form, and isolating the hypoglycosylated protein of interest from the fermented cell or cells, or from the culture supernatant.
18. A method of using the isolated mutant yeast strain according to claim 13 to produce a hypoglycosylated protein of interest, said method comprising fermenting a cell or cells of said strain under conditions to produce a protein of interest in a hypoglycosylated form, and isolating the hypoglycosylated protein of interest from the fermented cell or cells, or from the culture supernatant.
19. A method of using the isolated mutant yeast strain according to claim 14 to produce a hypoglycosylated protein of interest, said method comprising fermenting a cell or cells of said strain under conditions to produce a protein of interest in a hypoglycosylated form, and isolating the hypoglycosylated protein of interest from the fermented cell or cells, or from the culture supernatant.
20. A method of using the isolated mutant yeast strain according to claim 15 to produce a hypoglycosylated protein of interest, said method comprising fermenting a cell or cells of said strain under conditions to produce a protein of interest in a hypoglycosylated form, and isolating the hypoglycosylated protein of interest from the fermented cell or cells, or from the culture supernatant.
21. A method of using the isolated mutant yeast strain according to claim 11 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.
22. A method of using the isolated mutant yeast strain according to claim 12 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.
23. A method of using the isolated mutant yeast strain according to claim 13 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.
24. A method of using the isolated mutant yeast strain according to claim 14 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.

25. A method of using the isolated mutant yeast strain according to claim 15 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.

26. An isolated mutant yeast strain having defects in outer-chain N-glycosylation, said strain, when crossed with a strain of Saccharomyces cerevisiae selected from the group consisting of DSM 7042, DSM 7338, DSM 7160, and DSM 7340, yielding a diploid having defects in outer-chain N-glycosylation, said diploid, when transformed with a DNA encoding a protein of interest under conditions favoring expression of said protein, expressing said protein in hypoglycosylated form substantially without contamination with said protein in a form having outer-chain glycosylation, wherein said protein, when expressed in a wild-type yeast strain, is expressed in a form having outer-chain glycosylation.

27. A strain according to claim 26 wherein said strain yields said diploid when crossed with DSM 7042.

28. A strain according to claim 26 wherein said strain yields said diploid when crossed with DSM 7338.

29. A strain according to claim 26 wherein said strain yields said diploid when crossed with DSM 7160.

30. A strain according to claim 26 wherein said strain yields said diploid when crossed with DSM 7340.

31. A method of using the isolated mutant yeast strain according to claim 26 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.

32. A method of using the isolated mutant yeast strain according to claim 27 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.

33. A method of using the isolated mutant yeast strain according to claim 28 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.

34. A method of using the isolated mutant yeast strain according to claim 29 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.

35. A method of using the isolated mutant yeast strain according to claim 30 to produce a hypoglycosylated protein of interest, said method comprising transforming a cell or cells of said strain with a DNA encoding a protein of interest, and fermenting said transformed cell or cells under conditions to produce the hypoglycosylated protein of interest and isolating the hypoglycosylated protein of interest from the fermented cell or cells, or from the culture supernatant.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 1:

ATTTCTCCTT ATTGCGCGCT T          21

( 2 ) INFORMATION FOR SEQ ID NO: 2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 2:

TCTATTCAGC TGTCGACATA GATCTTATGT AATTTAGTTA CGCTTGAC    48

( 2 ) INFORMATION FOR SEQ ID NO: 3:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 3:

AGATCTATGT CGACAGCTGA ATAGATAAAA TTAGTGCGGA CTTTTTTTA    50

( 2 ) INFORMATION FOR SEQ ID NO: 4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 4:

GTCATTTGTA AAGTAAAATT CCAA    24

( 2 ) INFORMATION FOR SEQ ID NO: 5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 5:

GCCCGGTACC AGATCTATGC AGACTCTCCT TGTGAGCT    38

( 2 ) INFORMATION FOR SEQ ID NO: 6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

TCTAGAACTA GTGGATCCCC C     21

( 2 ) INFORMATION FOR SEQ ID NO: 7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 7:

GCCGGCGAAC GTGGCGAGAA     20

( 2 ) INFORMATION FOR SEQ ID NO: 8:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 8:

ATATATCAGC TGTCACTGCA TGCTAGCATA ATCTTCCAAG ATAGC     45

( 2 ) INFORMATION FOR SEQ ID NO: 9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 9:

CAGCACCACC ACCACTGACA G     21

( 2 ) INFORMATION FOR SEQ ID NO: 10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 10:

CTGTCAGTGG TGGTGGTGCT GCATG     25

( 2 ) INFORMATION FOR SEQ ID NO: 11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 11:

AGATCTATGT CGACAGCTCA ATAGA     25

( 2 ) INFORMATION FOR SEQ ID NO: 12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO: 12:

Gln His His His His
5